United States Patent
Gould et al.

(10) Patent No.: US 10,973,991 B2
(45) Date of Patent: Apr. 13, 2021

(54) INJECTION DEVICES

(71) Applicant: Owen Mumford Limited, Oxford (GB)

(72) Inventors: Oliver Gould, Oxford (GB); Tahir Shabudin, Oxford (GB); Matthew Farmer, Oxford (GB)

(73) Assignee: Owen Mumford Limited, Oxford (GB)

( * ) Notice: Subject to any disclaimer, the term of this patent is extended or adjusted under 35 U.S.C. 154(b) by 573 days.

(21) Appl. No.: 15/570,644

(22) PCT Filed: Feb. 18, 2016

(86) PCT No.: PCT/GB2016/050403
§ 371 (c)(1),
(2) Date: Oct. 30, 2017

(87) PCT Pub. No.: WO2016/174383
PCT Pub. Date: Nov. 3, 2016

(65) Prior Publication Data
US 2018/0296768 A1    Oct. 18, 2018

(30) Foreign Application Priority Data

Apr. 30, 2015  (GB) .................................... 1507491

(51) Int. Cl.
*A61M 5/32* (2006.01)
*A61M 5/20* (2006.01)
*A61M 5/31* (2006.01)

(52) U.S. Cl.
CPC .......... *A61M 5/326* (2013.01); *A61M 5/2033* (2013.01); *A61M 5/3202* (2013.01);
(Continued)

(58) Field of Classification Search
CPC .. A61M 5/326; A61M 5/2033; A61M 5/3202; A61M 5/3204; A61M 2005/2013
(Continued)

(56) References Cited

U.S. PATENT DOCUMENTS 5,335,802 A * 8/1994 Brach ................ B65D 47/0809
                                                        215/235
5,667,112 A * 9/1997 Verbruggen ......... B65D 47/061
                                                        222/539

(Continued)

FOREIGN PATENT DOCUMENTS

CN    2305204 Y    1/1999
EP    1529731 A1   5/2005
(Continued)

OTHER PUBLICATIONS

Search Report for GB Application No. 1507491.7, dated Nov. 2, 2015, 3 pages.

(Continued)

*Primary Examiner* — Phillip A Gray
(74) *Attorney, Agent, or Firm* — Quarles & Brady LLP

(57) ABSTRACT

The invention relates to an injection device comprising an elongate housing and a cap removably mounted over a forward end of the housing. The cap comprising at least one slot extending forwardly from its rear edge; the at least one slot being configured to engage with an outwardly projecting protrusion on an outer surface of the housing when the cap is mounted on the housing. A rearward portion of the cap includes rearwardly extending engagement features provided on each side of the at least one slot, the engagement features being configured to locate within a cavity in the housing when the cap is mounted on the housing. The cavity is provided with corresponding surfaces which align with the cap engagement features so as to hold the outwardly projecting protrusion within the cut-out.

18 Claims, 11 Drawing Sheets

(52) U.S. Cl.
CPC ..... *A61M 5/3204* (2013.01); *A61M 2005/206* (2013.01); *A61M 2005/2013* (2013.01); *A61M 2005/3125* (2013.01); *A61M 2005/3263* (2013.01)

(58) Field of Classification Search
USPC .......................................................... 604/197
See application file for complete search history.

(56) References Cited

U.S. PATENT DOCUMENTS

| | | | |
|---|---|---|---|
| 2007/0199933 A1 | 8/2007 | Salice | |
| 2011/0082428 A1 | 4/2011 | Huang | |
| 2015/0174325 A1* | 6/2015 | Young | A61M 5/2033 604/135 |

FOREIGN PATENT DOCUMENTS

| | | | |
|---|---|---|---|
| GB | 2478349 A | 9/2011 | |
| GB | 2494453 A | 3/2013 | |
| WO | WO2012085580 A1 | 6/2012 | |
| WO | WO2014009705 A1 | 1/2014 | |

OTHER PUBLICATIONS

International Search Report and Written Opinion for PCT Application No. PCT/GB2016/050403, dated Jun. 17, 2016, 14 pages.

\* cited by examiner

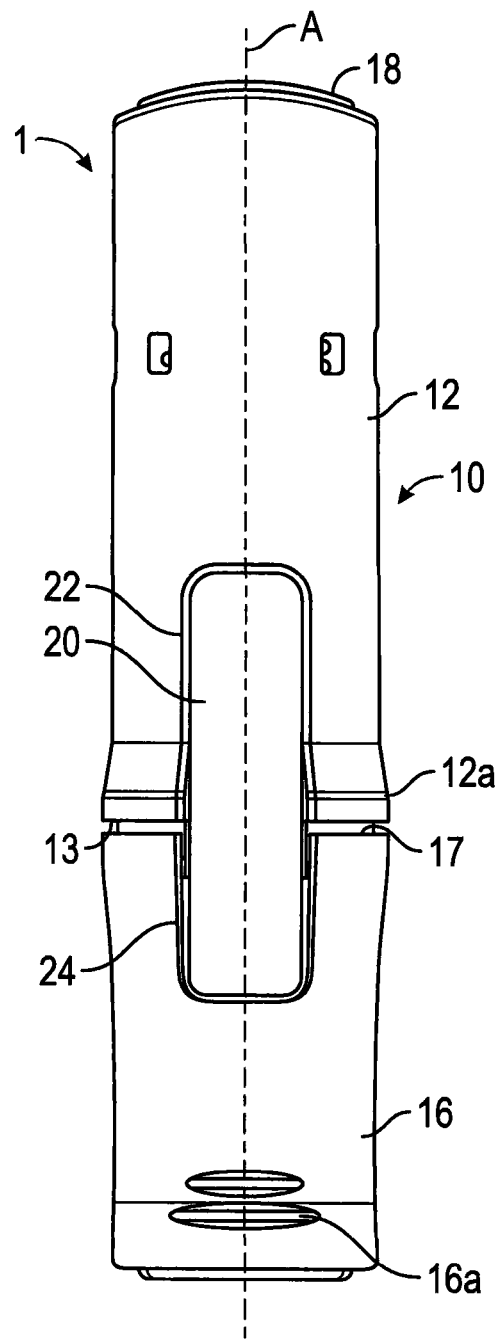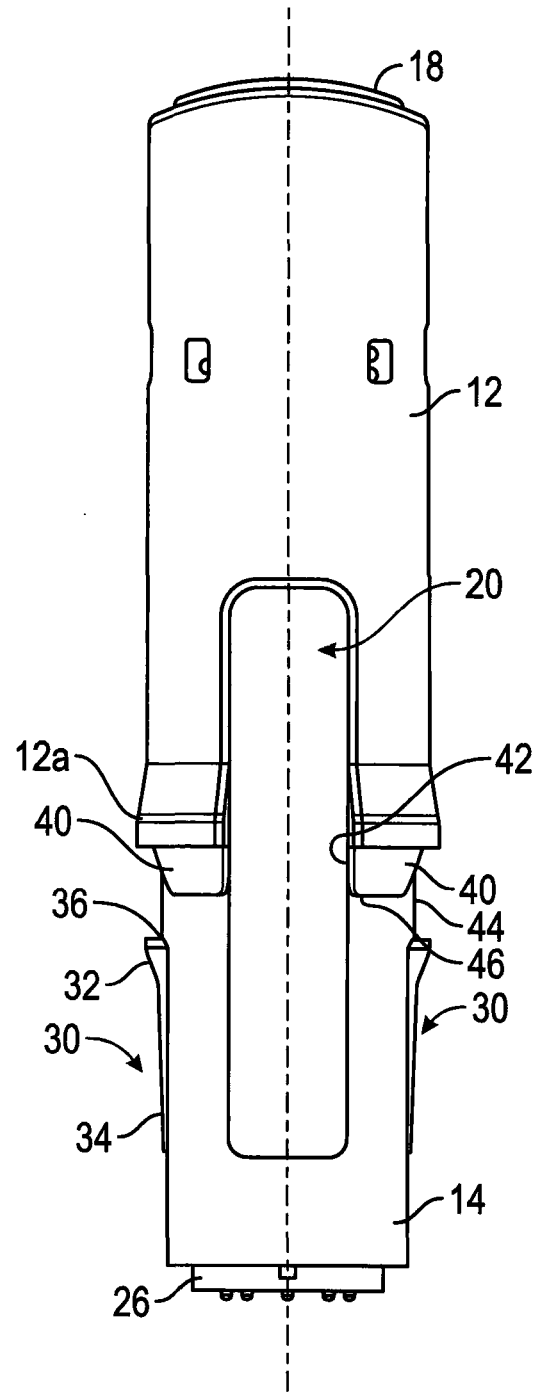
FIG. 1A
FIG. 1B

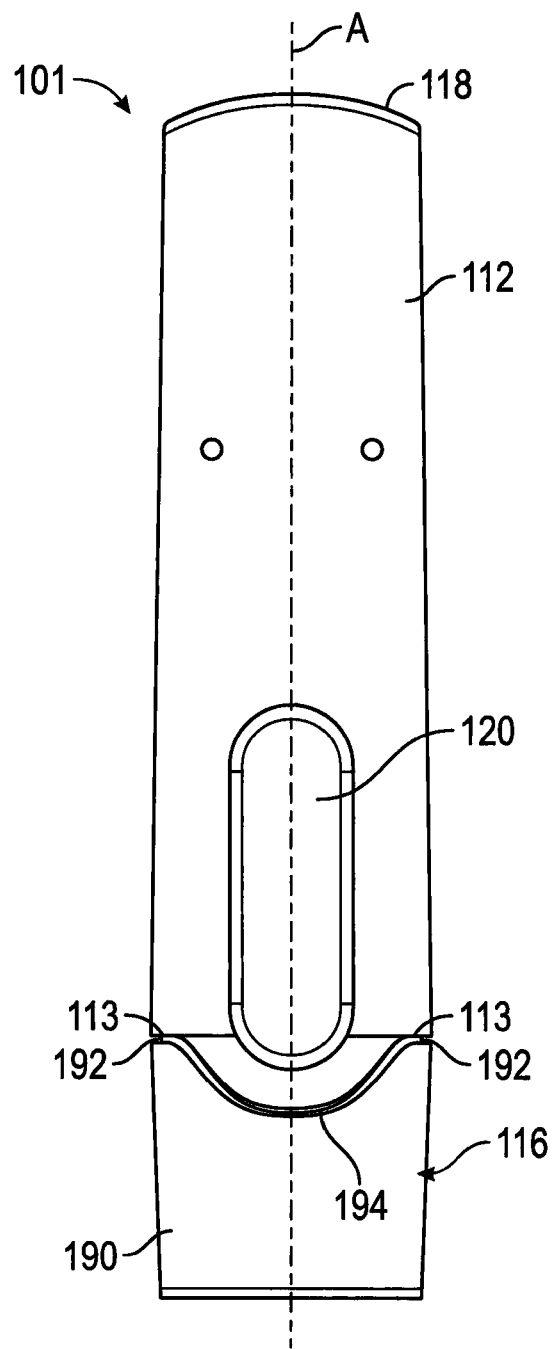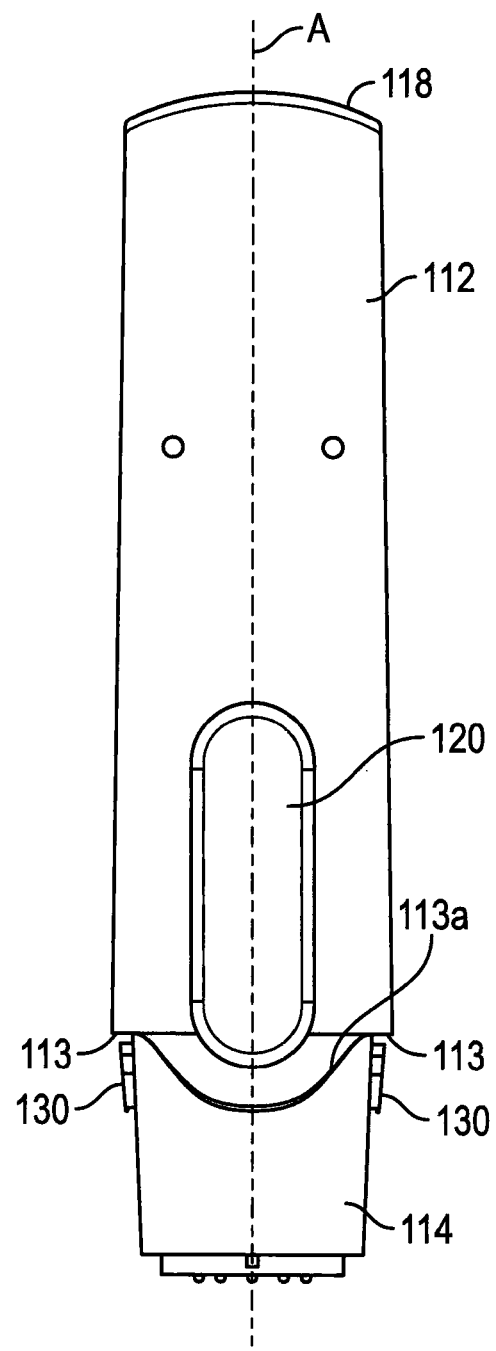
FIG. 5A  FIG. 5B

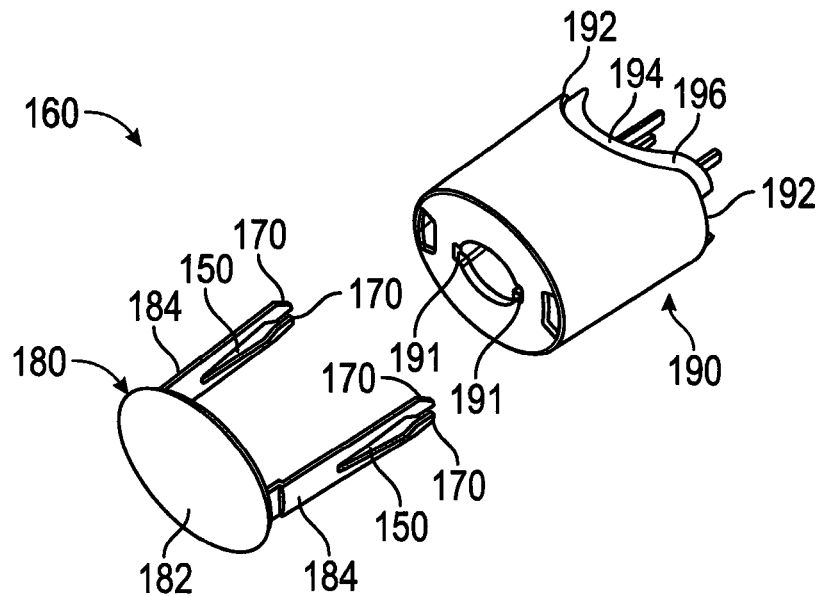
FIG. 9A
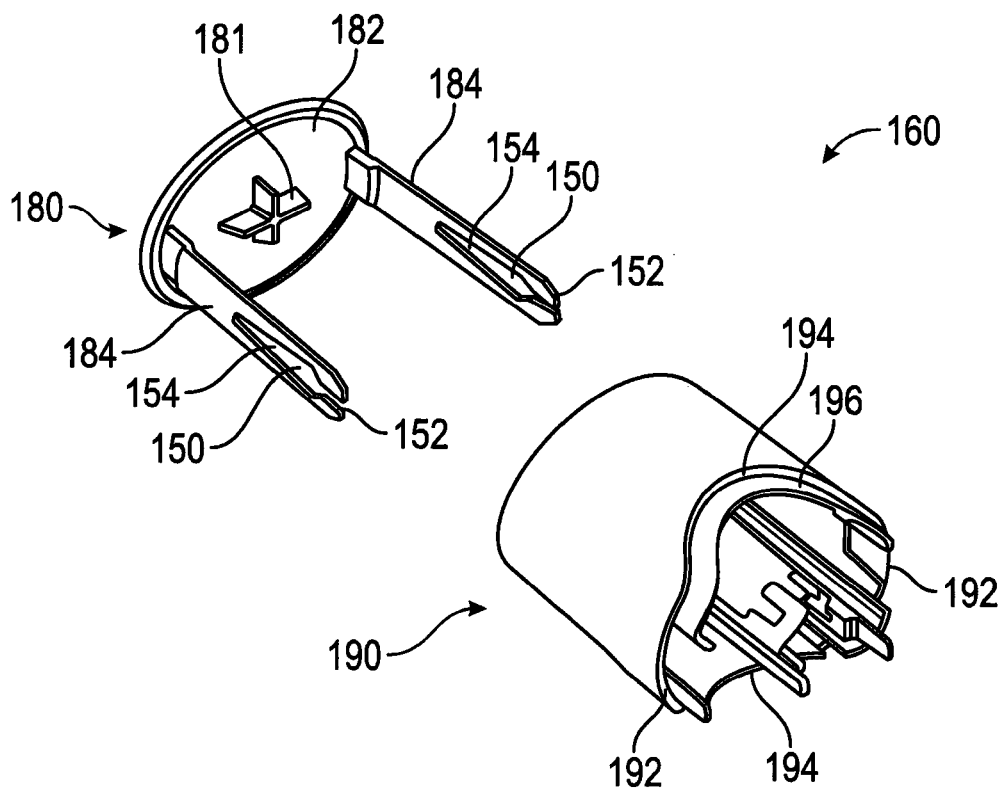

INJECTION DEVICES

CROSS-REFERENCE TO RELATED APPLICATIONS

This application represents the U.S. National Stage of International Application No. PCT/GB2016/050403 filed on Feb. 18, 2016, which is incorporated by reference in its entirety, and is based upon, claims priority to, and incorporates herein by reference in its entirety, United Kingdom Patent Application Serial No. GB 1507491.7, filed Apr. 30, 2015.

FIELD OF THE INVENTION

This invention relates to injection devices for delivering a dose of medicament from a syringe. In particular, but not exclusively the invention relates to an "autoinjector" device.

BACKGROUND OF THE INVENTION

Injection devices are used for the convenient administration of medicaments. For example, injection devices (which may typically be in the form of a pen injector) may be used for providing a single metered dose of a medicament, such as Epinephrine, in an emergency or for providing regular metered doses of a medicament, such as Insulin. Such devices may be either single use "disposable" devices in which the device is typically provided with a syringe already installed, and which is not user-replaceable, or "reusable" devices which allow the user to replace the syringe when the medicament has been used.

It may be noted that whilst the term "syringe" is used herein for clarity and consistency, this term is not intended to be limiting. In some arrangements the syringe may for example be a cartridge (which, for example, may be arranged to receive a disposable needle) or other medicament container. In some arrangements the syringe/cartridge/medicament container may formed integrally with the (or part of the) injection device.

Injection devices may be provided in the form of an "autoinjector" device in which, in addition to automating the delivery of the medicament, the device is also arranged to automate the insertion of a needle into the skin prior to the delivery of the medicament.

Injection devices generally comprise a delivery mechanism which is arranged to automatically deliver a dose from the syringe, and optionally (in the case of an autoinjector) to first displace the syringe within the housing to cause needle penetration. The delivery mechanism is typically released from an energised (or primed) position and may, for example, include one or more drive springs. The delivery mechanism may act upon a plunger which includes or acts against a piston (also referred to as a "bung") which is slidably provided within the syringe. In the case of an autoinjector the initial stiction between the piston and syringe may resist forward movement of the piston relative to the syringe such that initially the drive mechanism moves the syringe into the needle insertion position (whereupon further movement of the syringe is blocked and the drive mechanism will continue to move forward thus moving the piston).

Injection devices, such as autoinjectors, have a main elongate body having a forward end through which a needle extends during the injection. For safety reasons, they are generally provided with removeable caps that are mounted over the forward end of the main body to protect the user from accidental needle stick injury. Such caps must be held securely on the device. Known caps include inwardly projecting dimples on the inner surface the cap which engage with corresponding recesses on the outer surface of the main body. This type of arrangement only provides a reasonably light connection between the cap and injection device but the cap can easily be accidentally be removed, for example, when the device is dropped or banged against a surface, such as the floor. This may be a particularly important issue with pressure activated injection devices, in which the user presses a forward portion of the device against the injection site to release a mechanical interlock and fire the device. In pressure activation devices, a large impact can cause inertial forces within the device which release interlock and cause the device to fire unintentionally.

An improved cap connecting arrangement is described in the applicant's earlier Published International Patent Application WO2013/038166, in which two opposite sides of the main body of the device are provided with bulb shape projections, each projection having a rear neck portion and a wider head portion. The cap is provided with two correspondingly shaped and positions cut-outs. When the cap is mounted onto the body, each projection slides into and is received in the corresponding cut-outs, thereby holding the cap on the body. Embodiments of the invention seek to provide further improvements over this arrangement.

Embodiments of the invention seek to provide needle shield assemblies which overcome some or all of these problems.

SUMMARY OF THE INVENTION

Accordingly, in one aspect, this invention provides an injection device comprising:

a housing;

a cap removably mounted over a forward end of the housing; the cap comprising at least one slot extending forwardly from its rear edge; the at least one slot being configured to engage with an outwardly projecting protrusion on an outer surface of the housing when the cap is mounted on the housing;

wherein a rearward portion of the cap includes rearward extending engagement features provided on each side of the at least one slot, the engagement features being configured to locate within a cavity in the housing when the cap is mounted on the housing;

wherein the cavity is provided with surfaces which align with the cap engagement features to prevent, or limit, the side walls of the at least one slot from splaying outwardly when the cap engagement feature are located within the cavity, so as to hold the outwardly projecting protrusion within the cut-out.

Whilst a separate cavity may be provided for receiving each engagement feature, conveniently a single cavity may receive the engagement features provide on both sides of a slot. The housing may be an elongate housing.

The rearward extending engagement features may comprise rearward extending engagement surfaces. The cavity may comprise corresponding forward facing mating surfaces, for example two facing mating surfaces.

When cap is connected to the injection device in its fully rearward position the positioning of the engagement features within the cavity limits the outward movement of the side walls of the slot. In contrast when the cap is removed by a user it is pulled forwardly and the engagement features move out of the cavity to allow the side walls of the slot to displace outwardly. Further, if the cap moves rearwards, for example when the cap is subjected to a sudden shock load or impact, the forwarding facing mating surfaces of the cavity engage with the cap engagement features, and the two side walls of the slot are urged together and are prevented from moving outwardly or apart from each other. This means that the outwardly projecting protrusion is prevented from being released from the cap slot and the cap is held or retained on the housing.

The cavity may be a forward facing cavity. The outwardly projecting protrusion on the housing may extend from the housing in a generally radial direction. The slot may include two side or laterally extending walls which engage two lateral sides of the outwardly projecting protrusion.

The cavity may include two side walls which form the forwardly facing mating surfaces. The cavity may also include a rear wall extending between the two side walls.

According to another aspect, the invention provides an injection device comprising:

a housing;

a cap removably mounted over a forward end of the housing and comprising at least one slot extending forwardly from a rear edge of the cap; the at least one slot being configured to engage with an outwardly projecting protrusion provided on an outer surface of the housing when the cap is mounted on the housing;

wherein the rearward portion of the cap comprises portions on opposing sides of the slot, at least one of portion being resiliently deformable;

the housing further comprises a forward facing mating surface aligned with rearward facing engagement surfaces on the at least one resiliently deformable portion when the cap is mounted thereon, and wherein the forward facing mating surfaces and rearward facing surface of the at least one resiliently deformable portion are profiled such that when the surfaces are urged together the at least one resiliently deformable portion is cammed inwardly relative to the slot to restrict or reduce the effective width of the slot.

The rearward cap may comprise resiliently deformable portions are on opposing sides of the slot.

Such an arrangement may advantageously ensure that a force urging the cap and housing together may wedge the resiliently deformable sides of the slot together, thereby reducing the width of the slot, and cause the cap to in effect grip the protrusion and hold the cap on the housing. This arrangement may prevent the cap from being accidentally or intentionally removed from the housing when a force is applied to the cap, for example, when an injection device is accidentally dropped on its forward end and the cap is urged towards the housing.

This arrangement may also advantageously ensure that an internal force generated within the housing pushing the cap forward may initially urge the rearward mating surfaces outwards towards the forward mating surfaces of the housing until the rearward mating surfaces contact and are restrained by the forward mating surfaces, thereby restricting the width of the slot and causing the cap in effect to grip the protrusion. This arrangement may prevent the cap from being accidentally or unintentionally removed from the housing when an impact or shock load is applied to a rear end or a trigger button of the device. For example, when an injection device is accidentally dropped on its rear end and a forward housing component comprising the outwardly projecting protrusion may be urged momentarily forward. This arrangement may also prevent the cap from being accidentally or unintentionally removed from the housing when an impact or shock load is applied to the device which is sufficient to cause inertial forces within the device which release an interlock within the housing. The resiliently deformable portions may define at least a rearward portion of the slot. The resiliently deformable portions may be cammed inwardly relative to the slot to reduce the effective width of the slot at the rearward end (or neck) of the slot.

The forward facing mating surface may abut with the rearward facing engagement surfaces on the resiliently deformable portions when the cap is mounted thereon.

A rearward portion of the slot may be arranged to have a transverse clearance gap relative to the protrusion when the cap is attached to the housing. For example the slot may extend rearwardly beyond the protrusion when the cap is mounted on the housing. Alternatively, the rear of the outwardly projecting protrusion may be profiled. For example the protrusion may have a narrow or tapered rear end. The protrusion may, for example, narrow to a greater extent than the corresponding portion of the slot (when the cap is mounted on the housing). As a result when the surfaces are urged together, the side walls of the slot rearwardly of the protrusion (or of the main portion of the protrusion) can move inwards with respect to each other.

The rearward facing engagement surfaces on the cap may have a sloped or angled profile. The forward facing mating surfaces on the housing may have a sloped or angled profile. The rearward facing engagement surfaces on the cap and the forward facing mating surfaces may have corresponding profiles, configured such that as the cap is mounted onto the housing and pushed rearward, the surfaces are urged together.

The rearward facing engagement surfaces on the cap may have a curved or straight profile. The forward facing mating surfaces have a curved or straight profile. The rearward facing engagement surfaces on the cap and the forward facing mating surfaces may have corresponding profiles or shapes configured such that as they are urged together, the resiliently deformable portions are cammed inwardly relative to the slot to reduce the effective width of the slot.

The cap may include at least one, preferably two, engaging arms. The engaging arms may extend rearward from a rear edge of the cap on opposing sides of the slot. Each arm may have a first surface extending from the at least one slot, preferably extending continuously from a slot side wall. Each arm may have a second, outer sloped surface.

The forward facing mating surfaces may have an angled (or sloped) profile. The cavity may include two side walls which define the forward facing mating surfaces. The cavity may include a forward facing wall at its rear end, extending between the two forward facing mating surfaces.

The first surface of the engaging arm may extend from and define at least a rearward portion of the slot. The first surface of the engaging arm may extend continuously from a narrow, neck portion of the slot.

The slot may include a rear neck portion extending from a rear edge of the cap, leading to a locating portion having a maximum width greater than that of the neck portion. The outwardly projecting protrusion may have a maximum width which substantially corresponds to the maximum width of the slot locating portion.

The outwardly projecting protrusion may have a geometry or outline which substantially corresponds to the geometry or outline of the locating portion. The outwardly projecting protrusion may be elongate. The locating portion may be elongate.

The region of the slot wall between the neck and locating portions may have a sloped or curved profile. The rear end of the outwardly projecting protrusion may be tapered or narrowed, so that as the cap is removed from the housing the rear end of the protrusion pushes open the slot neck portion of the slot which allows the protrusion to slide out of the cut-out.

The outwardly projecting protrusion may be elongate. The outwardly projecting protrusion may include a rear portion which projects further outwards from the housing than the forward portion.

The outwardly projecting protrusion may have a substantially flat outer surface. The outwardly projecting protrusion may have an outer surface which is a continuous slope in the longitudinal direction. The rear portion surface may extend at a first angle to a general longitudinal axis of the device. The forward portion surface may extend at a second angle to the general longitudinal axis, the second angle being smaller than the first angle. The outwardly projecting protrusion may have a T-shape cross section, having a beam extending outward from the outer surface of the housing and an outer surface perpendicular to the beam.

The cap may comprise an outer body, and an insert which is mounted at least partially within the outer body to assemble the cap. The slot is provided in the insert portion.

The insert may includes a forward portion; and two engaging arms which extend rearwardly from the forward portion. The opposing surfaces of the arms may form the slot. Each arm may have an first surface extending from the at least one slot and a second, outer sloped surface. The rearward tips of the arms may extend rearwardly from a rear edge of the cap outer body on opposing sides of the slot.

The slot may includes a rear neck portion extending from a tip of the insert, leading to a locating portion having a maximum width greater than that of the neck portion. The outwardly projecting protrusion may have a maximum width which substantially corresponds to the maximum width of the slot locating portion.

The insert may include two pair of engaging arms. The two pairs of engaging arms may be provided on diametrically opposing sides of the insert.

The insert may include two separate components which are mounted at least partially within the outer body to assembly the cap. Each component having a pair of engaging arms.

The housing may include a rear body portion and a front body portion. The rear body portion may be mounted to or over a rear end of the front body portion. The outwardly projecting protrusion may be provided on the front body portion. The forward facing mating surfaces may be provided on the rear body portion. The cavity may be provided on a forward edge of the rear body portion.

The cap may include a rear edge which contacts a forward abutment surface on the rear body portion when the cap is mounted on the housing.

The rear of the cap is provided with an undercut on both sides of the slot. The rear body portion may be provided, on both sides of the cavity, with a reduced diameter projection extending forwardly from the abutment surface and configured such that when the cap is mounted on the housing, the reduced diameter projection locates within the corresponding undercut.

The reduced diameter projections may be held in the undercuts when the cap is mounted. This prevents the front of rear body housing splaying outwardly and holds the mating surfaces of the cavity against the cap engagement surfaces.

The engaging arms may extend rearwardly from the rear of the undercut. The cavity may include two side walls. The reduced diameter projections may extend forwardly from the cavity side walls. The engaging arms may extend continuously from the rear of the undercut. The reduced diameter projections may extend continuously from the cavity side walls.

The cap may be provided with two slots extending forwardly from a rear edge of the cap. The outer surface of the housing may be provided with two corresponding outwardly projecting protrusions. The two slots may be provided on opposite sides of the cap. The two slots may be provided on diametrically opposing sides of the cap.

The slots and protrusions may be symmetrical, which means that each may engages with either of the outwardly projecting protrusions when the cap is mounted on the housing.

The housing may include a rear body portion and a front body portion, the rear body portion being slideable relative to the front portion. For example the housing portions may be relatively slideable in order to activate delivery of a medicament and/or to disengage an interlock. Embodiments of the invention may be particularly useful in such arrangements as forward movement of the rear body portion may, in prior art arrangements, act to push the cap from the forward end of the device. Further, embodiments of the invention may advantageously providing an arrangement in which the cap actively blocks forward movement of the rear body portion (for example by effectively gripping the protrusion) in the event that the rear housing is urged forward relative to the cap (which is fixed relative to the forward housing). For example, such forces may be encountered due to inertia if the device is dropped and strikes the floor. In contrast, when removing the cap to prepare the device for use the cap and rear housing portion are urged apart so embodiments of the invention will not impede removal of the cap.

The housing or the cap may include first and second cut-away regions. The elongate housing and the cap may include first and second cut-away regions, which when the cap is mounted on the housing are aligned to define a viewing window through which at least a part of a syringe or cartridge mounted inside the housing can be viewed.

The viewing window or viewing aperture may comprise a plurality of aligned windows or apertures formed in the components of the injection device which surround a syringe or barrel mounted inside the housing. For example windows or apertures may be formed in the housing and the syringe carrier. At least one of the windows or apertures may be a transparent window (for example the outer housing). Cut away regions may be provided on diametrically opposite sides of the device.

The housing may include a cut away region which defines a viewing window through which at least a part of a syringe or cartridge mounted inside the housing can be viewed. The cap may include a reward facing recess. The housing may include a forward projecting portion which engages with a rear facing recess on the cap when the cap is mounted on the housing. The cut-away region may provided at least partial in the forward projecting portion on the housing.

The housing may include two cut away regions on diametrically opposite sides of the housing. The housing may include a forward abutment surface for engaging with a rear edge of the cap; and a forward projection which extends forwardly of the forward abutment surface. The cut-away region may be provided at least partially in the forward projection. The housing may include two forward projections and two cut-out regions provided at least partially in the forward projections. The housing may include a rear body portion and a front body portion, the rear body portion being slideable relative to the front portion. The forward projection(s) may be provided on the rear body.

A further advantage of any of the embodiments of the invention is that after the cap is removed from the device by a user, the arrangements described above may also ensure that the cap cannot be easily reattached to the device.

Whilst the invention has been described above, it extends to any inventive combination of the features set out in the following description or claims or drawings.

BRIEF DESCRIPTION OF THE DRAWINGS

The invention may be performed in various ways and an embodiment thereof, with various modifications, will now be described by way of example only, reference being made to the accompanying drawings in which:

FIG. 1A is an injection device according to a first embodiment of the invention;

FIG. 1B is the injection device of FIG. 1A with the cap removed, in a pre-injection state;

FIG. 5A is an injection device according to a first embodiment of the invention;

FIG. 5B is the injection device of FIG. 1A with the cap removed, in a pre-injection state;

FIGS. 9A and 9B are exploded view of the cap of the second embodiment.

DESCRIPTION OF EMBODIMENTS

Figure 2A:
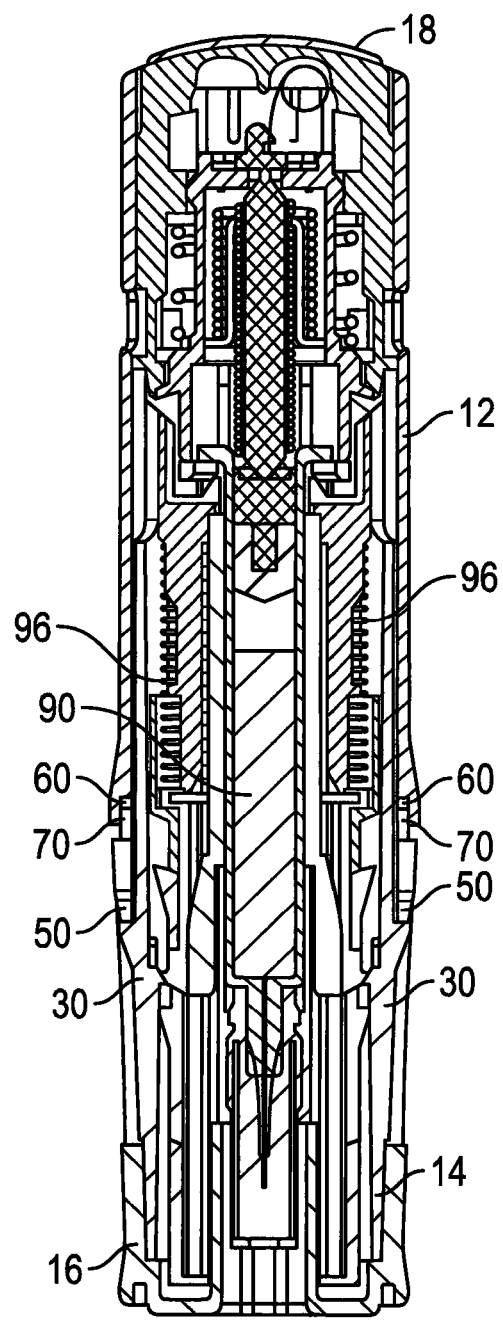
FIG. 2A is a cross-sectional view through the central longitudinal axis of FIG. 1A.

Front as used herein will be understood to refer to the end of the injector assembly (or components thereof) which, in use, are closest to the delivery needle delivery end of the injector (i.e. the end which is pointed at the skin). Rear as used herein will be understood to refer to the end of the pen injector assembly (or components thereof) which, in use, are furthest from the needle delivery end of the injector (i.e. the end which is pointed away from the skin). Forward and rearward will, likewise, be understood to refer to the directions orientated towards the front and rear of the injector assembly.

Axial, radial and circumferential are used herein to conveniently refer to the general directions relative to the longitudinal direction of the injection device (or components thereof). The skilled person will, however, appreciated that these terms are not intended to be narrowly interpreted (and for example, the injection device may have a non-circular and/or irregular form). Typically, regardless of the chosen injector device external profile the cartridge or syringe will have a conventional generally cylindrical form and, as such, the longitudinal axis of the injection device will substantially coincide with (or be parallel to) the axial direction of the syringe.

FIGS. 1A and 1B show front views of an injector device in accordance with an embodiment of the invention. The injection device 1 includes a housing 10 having a rear body portion 12 and a front body portion 14, and a removable cap 16 mounted over the forward end of the front body portion 14. The rear body portion 12 is mounted over a rear end of the front body portion 14, and the rear body portion 12 is slideable relative to the front portion 14 in order to disengage an interlock (described later). A rear edge 17 of the cap 16 contacts a forward abutment surface 13 on the rear body 12 when the cap 16 is mounted on the housing. The cap 16 includes a gripping surface 16a to facilitate cap removal.

The embodiment shown has an oval cross-sectional shape. However, the skilled person would appreciate that injection devices may have other cross-sections, such as for example, a circular or a polygon.

The embodiment shown includes a trigger button 18. However, the skilled person would appreciate that in some injection devices the device may be pressure activated, i.e. the activation trigger is activated when a front portion of the device is pressed against the injection site, and therefore, such a device does not include a trigger button.

The rear body portion 12 includes a cut-out 22 and the cap 16 includes a cut out 24. When the cap 16 is mounted (FIG. 1A), the two cut-outs 22, 24 define a viewing window 20 through which at least a part of a syringe or cartridge (not shown in FIGS. 1A and 1B) mounted inside the housing can be viewed.

Figure 2B:
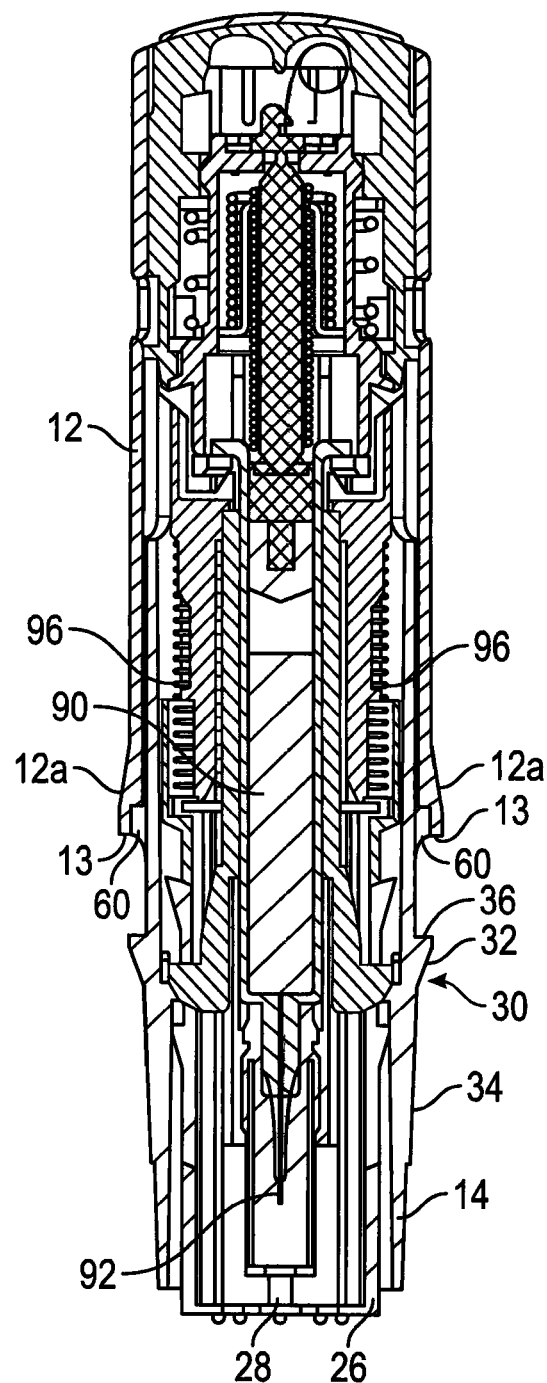
FIG. 2B is a cross-sectional view through the central longitudinal axis of FIG. 1B.

Slideably mounted within the front body 14 is a needle shroud 26 having an aperture 28 in its front face, through which a needle 92 of a syringe 90 may project during an injection (FIGS. 1B, 2A and 2B). A syringe carrier 94 is slideably coupled to the shroud 90. The device 1 also includes a pair of shroud springs 96 (FIGS. 2A and 2B). It may be noted that the features of the shroud 90, syringe carrier 94 and springs 96 as described above are substantially similar to that of WO2012/085580A1. The injection device of this embodiment also includes a drive mechanism (seen in FIGS. 2A and 2B) which is not described in detail here (as the particular arrangement is not essential to the invention), but is substantially of the type disclosed in the applicant's application WO2012/085580A1.

Figure 3A:
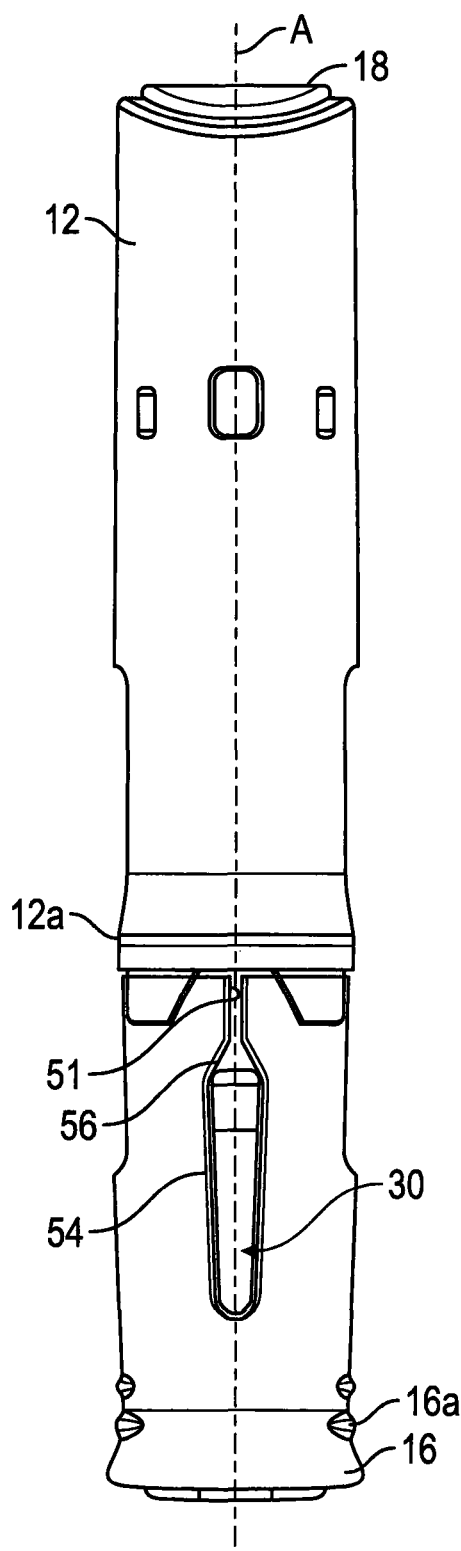
FIG. 3A is a side view of the injection device of FIG. 1A.
Figure 3B:
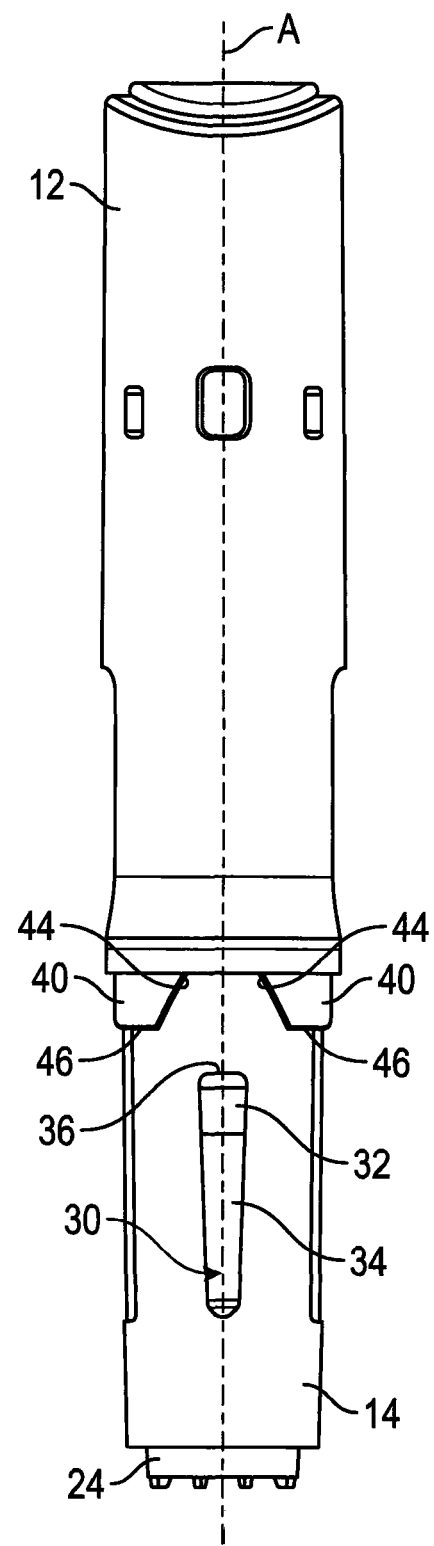
FIG. 3B is a side view of the injection device of FIG. 1B.

In this embodiment, the injection device is substantially symmetrical when viewed from the front (FIGS. 1A and 1B). FIGS. 3A and 3B show the injection device when viewed from one side, although it is appreciated that this view is the same for each side of the device.

Two outwardly projecting protrusions 30 are provided on the outer surface of the front body 14. The protrusions 30 are provided on diametrically opposite sides of the front body 14 and they extend in a generally radial direction. In this embodiment they are provided at opposite sides of the large diameter of the oval cross-section of the front body 14. The protrusions 30 are elongate and extend substantially parallel to a central longitudinal axis A through the device. The protrusions 30 extend along a central part of the front body 14. Each protrusion 30 includes a rear portion 32 and a forward portion 34. A rear end wall 36 extends substantially perpendicular to the outer surface of front body 14. The rear portion 32 has a substantially flat outer surface which extends at a first angle to the outer surface of the front body 14. The front portion 34 has a substantially flat outer surface and extends at a second angle to the outer surface of the front body 14, the second angle being smaller than the first angle. The rear end of the protrusion 30 is narrowed or tapered (FIG. 4A).

The cap 16 includes two slots 50 extending forwardly from the cap rear edge 17 (FIGS. 1A and 3A). Each slot 50 includes two side walls 51 which extend rearwardly and define: a narrow neck portion 52 which extends from the cap rear edge 17, an elongate locating portion 54 having a maximum width greater than that of the neck 52, and an intermediate portion 56 joining the neck and locating portions 52, 54. The neck portion 52 extends substantially longitudinally and expands out (intermediate portion 54) forwardly into the locating portion 56. When the cap 16 is mounted (FIGS. 2A and 3A), one of the outwardly projecting protrusions 30 is located within the locating portion 54. The slot locating portion 56 is longer than the protrusion 30 in a longitudinal direction, this means that when the cap 16 is mounted onto the housing 10, the slot extends rearwardly beyond the protrusion 30.

A forward portion 12a of the rear body 12 has a larger or expanded diameter, and two forward facing cavities 60 are formed by a recess or undercut in the rear body forward portion 12a (see FIG. 2B). Each cavity 60 extends rearwardly from the forward abutment surface 13 of the rear body 12. Each cavity 60 is defined by two angled side walls 62 extending rearwardly from the rear body abutment surface 13; and a rear wall 64 extending between the two side walls 62 (see FIG. 4A). The angled side walls 62 rearwardly converge. Therefore, the cavity 60 has a forward opening or mouth which is wider than the cavity rear wall 64

Figure 4A:
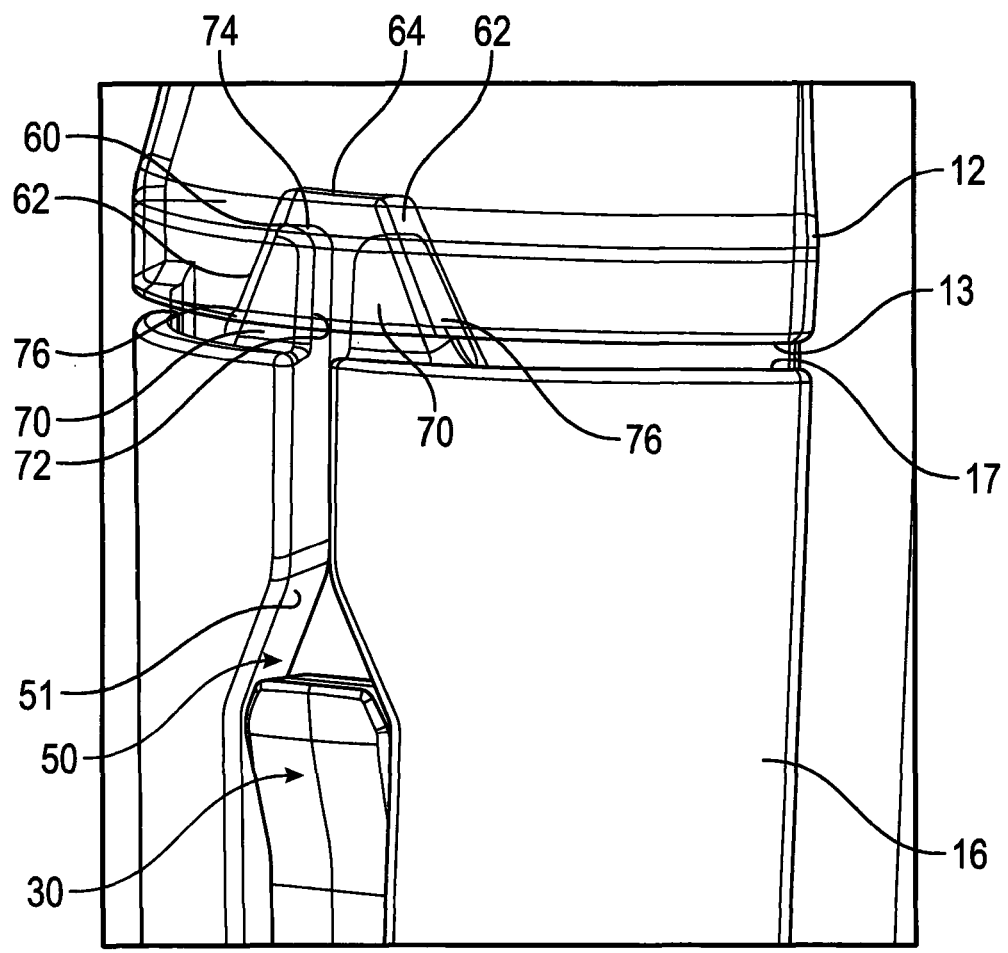
FIGS. 4A and 4B are detailed three-dimensional representations of the rear end of the cap and the central portion of the housing according to the first embodiment of the invention.

As shown in FIG. 4A, the cap 12 includes engaging arms 70 which extend rearwardly from the cap rear edge 17 on either side of the slot 50. Each engaging arm 70 includes a first wall 72 extending continuously from a side wall 51 of the slot 50, a tip 74, and a second wall 76 which is sloped or angled from the tip 74 to the cap rear edge 17.

When the cap 16 is mounted onto the housing, the second wall 76 forms a rearward facing engagement surface which engages with a corresponding forward facing mating surface formed by a cavity side wall 62. The engaging arms act 70 as resiliently deformable portions which are urged together by the cavity side walls 62 when the cap 16 is urged rearward on the housing (described in more detail below).

The rear body 12 includes reduced diameter elements 40 extending forwardly from the forward abutment surface 13 on the rear body 12. The elements 40 extend forwardly over the front body 14. Each element 40 includes a first side wall 42 which extends continuously longitudinally from a side wall of the cut-out 22; a second side wall 44 which is angled or sloped which extends from a side wall 62 of the cavity 60 (FIGS. 3B 4B), and a forward wall 46. The elements 40 have a substantially smooth outer surface.

Figure 4B:
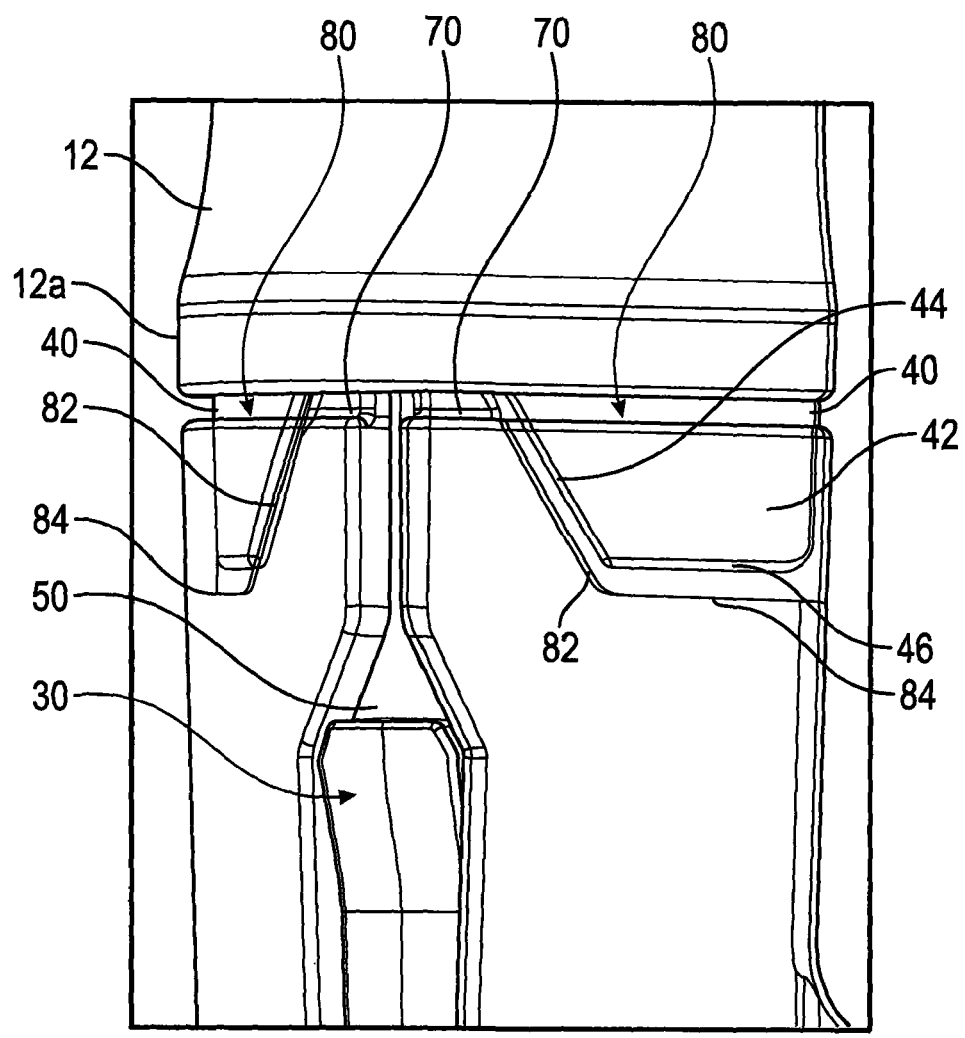

The rear cap 16 includes undercuts 80, extending forwardly from the cap rear edge 17 (FIG. 4B). Each undercut 80 is defined by a forward wall 84 and an angled side wall 82. The angled side wall 82 extends continuously from and is aligned with the engaging arm second wall 76 (FIG. 4B).

To mount the cap 16 onto the housing 10, the slots 50 are aligned with the protrusions 30. As cap 16 is pushed onto the housing, the slots 50 are pushed into engagement with the forward end of the protrusions 30, the slot necks 52 are opened outwards allowing the cap 16 to move rearwards. The cap 16 is pushed rearwards until the cap rear edge 17 contacts the rear body abutment surface 13. When the cap 16 is in the mounted position, the protrusions 30 are fully located within the slot locating portions 56, the engagement arms 70 are located within the cavity 60 and the reduced diameter portions 40 are located within the cap undercuts 80.

If the device 1 is subjected to an impact force that urges the cap and housing together, such as being dropped on its forward end on a hard surface such as the floor, the cap 16 is urged rearwardly against the rear body portion 12 (and the rear body may be urged forward by inertia). As such, the engagement surfaces 76 on the engagement arms 70 are urged against forward facing mating surfaces 62 in the cavity 60. This prevents the side walls 51 of the slot 50 from splaying outward which means that the protrusions 30 are firmly retained within the slots 50. Since the reduced diameter projections 40 are held in the cap undercuts 80, the front of rear body housing is also prevented from splaying outwardly, which keeps the mating surfaces 62 of the cavity 60 in contact with the cap engagement surfaces 76.

If the device 1 is subjected to an impact force which causes an internal force generated within the housing urging the forward body 14 forwards, such as being dropped on its rear end or a trigger button, the protrusions 30 on the forward body 14 move forwardly and initially act on the side walls of the slot 50. If sufficient internal force is generated in the device, the side walls 51 of the slot 50 may initially splay outwards until the cap engagement surfaces 76 contact with and are restrained by the mating surfaces 62 of the cavity 60. This limits the movement of the side walls 51, prevents them from splaying further which means that the protrusions 30 remain firmly retained within the slots 50. Since the reduced diameter projections 40 are held in the cap undercuts 80, the front of rear body housing is also prevented from splaying outwardly, which keeps the mating surfaces 62 of the cavity 60 in contact with the cap engagement surfaces 76.

Since the cap engaging arms 70 are held in the rear body cavity 60 and the rear body reduced diameter portions 40 are held in the cap undercuts, this provides an overlapping and interwoven arrangement between the cap 16 and rear body portion 12. The overlapping elements of the rear body 12 and cap 16 are urged against each other to prevent the cap 16 and rear body 16 moving with respect to each other.

To remove the cap 16 from the housing 10, the user pulls the cap 16 away from the housing 10 and the engaging arms 70 move rearwardly out of the cavity 60. The rear tapered end of the protrusion 30 engages with the neck of the slot 50. Since the engaging arms 70 are now aligned with the wider, forward part of the cavity 60, the slot side walls 51 are able to splay outwardly allowing the protrusion 30 to pass through the neck 52, so that the cap 16 can be removed. FIGS. 5A and 5B show front views of an injector device in accordance with a second embodiment of the invention. The injection device 101 includes many components which are substantially the same as the earlier embodiment, and similar reference signs are used for consistency. However, as explained in more below, this embodiment has an alternative interface between the housing and cap.

The injection device 101 includes a housing 110 having a rear body portion 112 and a front body portion 114, and a removable cap 116 mounted over the forward end of the front body portion 114. The rear body portion 112 is mounted over a rear end of the front body portion 114, and the rear body portion 112 is slideable relative to the front portion 114 in order to disengage an interlock. A trigger button 118 is provided at the rear of the device.

As with the earlier embodiment, the device shown in the Figures has an oval cross-sectional shape. However, the skilled person would appreciate that injection devices may have other cross-sections, such as for example, a circular or a polygon.

Figures 6A, 6B:
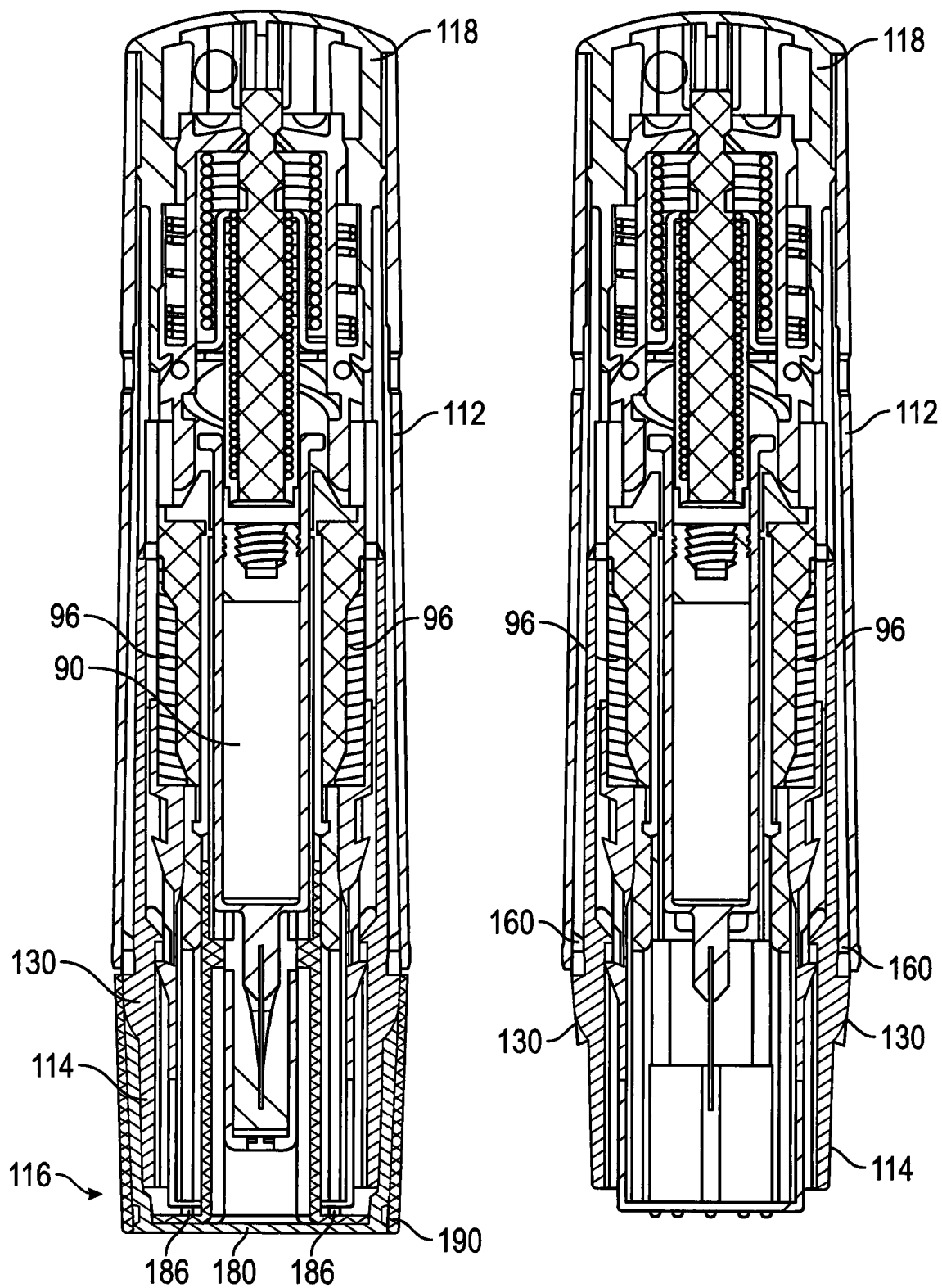
FIG. 6A is a cross-sectional view through the central longitudinal axis of FIG. 5A.
FIG. 6B is a cross-sectional view through the central longitudinal axis of FIG. 5B.

The cross-sectional views (FIGS. 6A and 6B) show the internal components of the device which are substantially the same as shown and described in the earlier embodiment (and are given corresponding reference numbers for consistency) and are of the type disclosed in the applicant's application WO2012/085580A1.

Figure 7A:
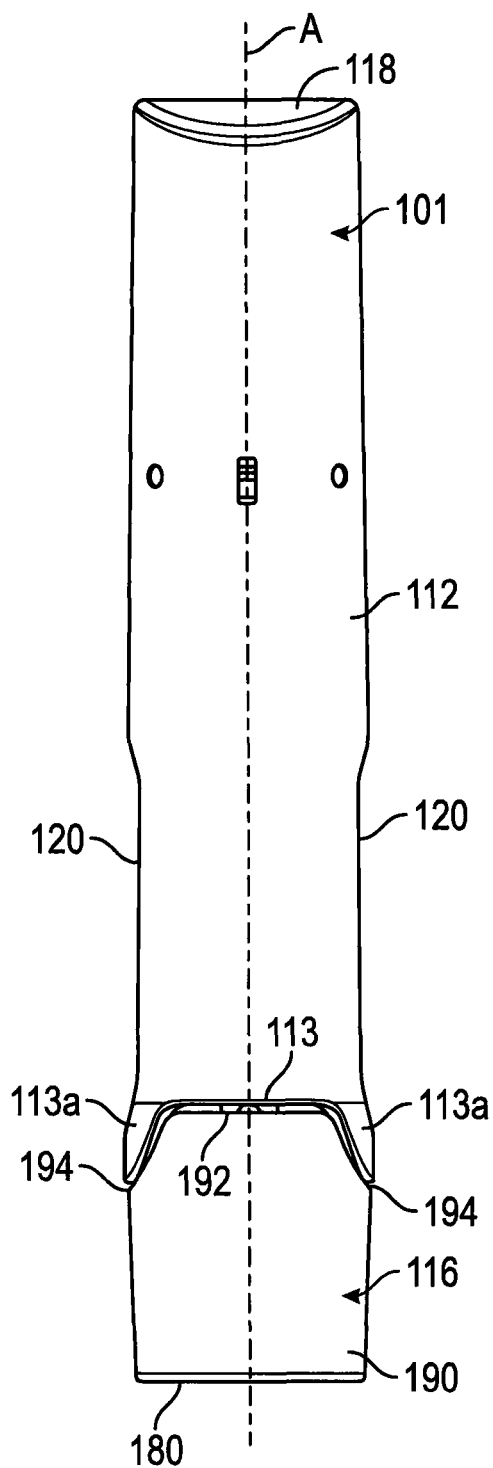
FIG. 7A is a side view of the injection device of FIG. 5A.
Figure 7B:
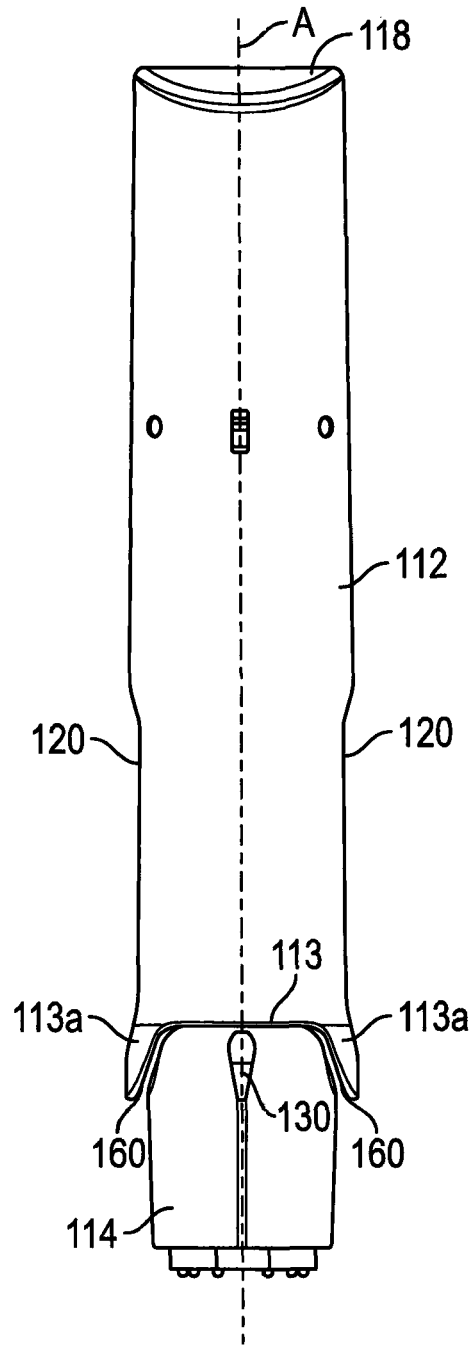
FIG. 7B is a side view of the injection device of FIG. 5B.

In this embodiment, the injection device is substantially symmetrical when viewed from the front (FIGS. 5A and 5B). FIGS. 7A and 7B show the injection device when viewed from one side, although it is appreciated that this view is the same for each side of the device.

Figure 8A:
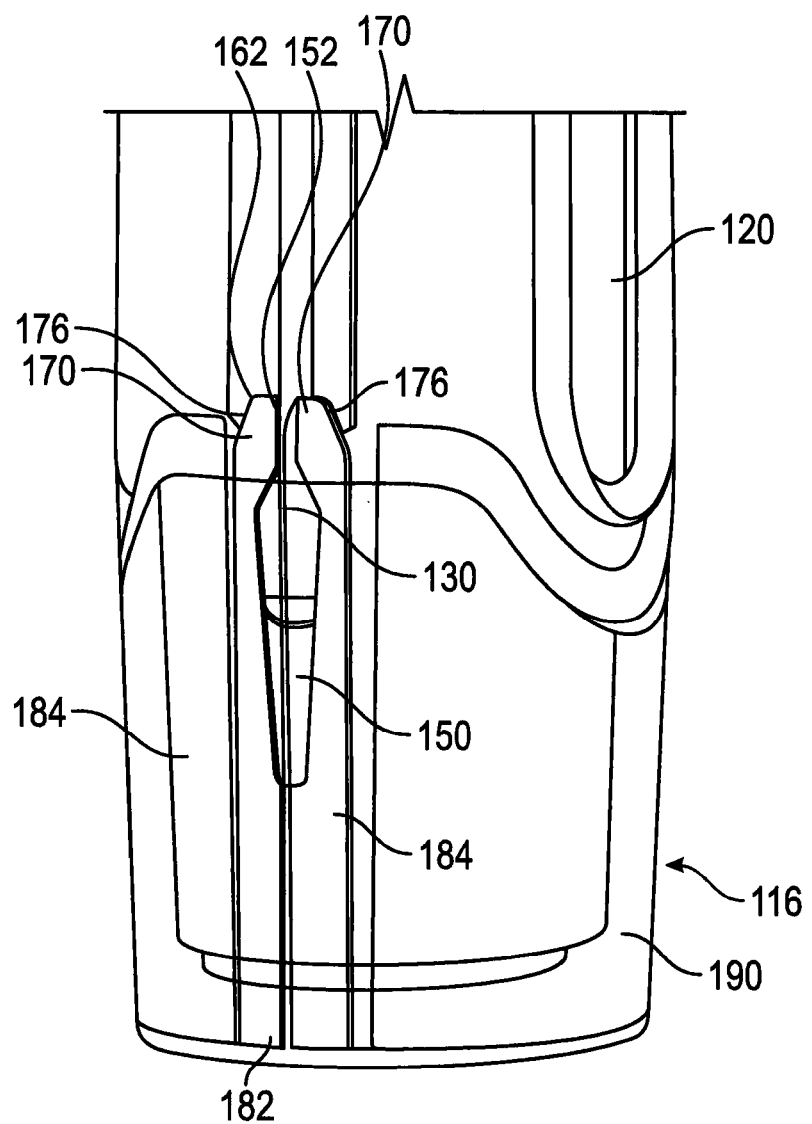
FIGS. 8A and 8B are detailed three-dimensional representations of the rear end of the cap and the central portion of the housing according to the second embodiment.
Figure 8B:
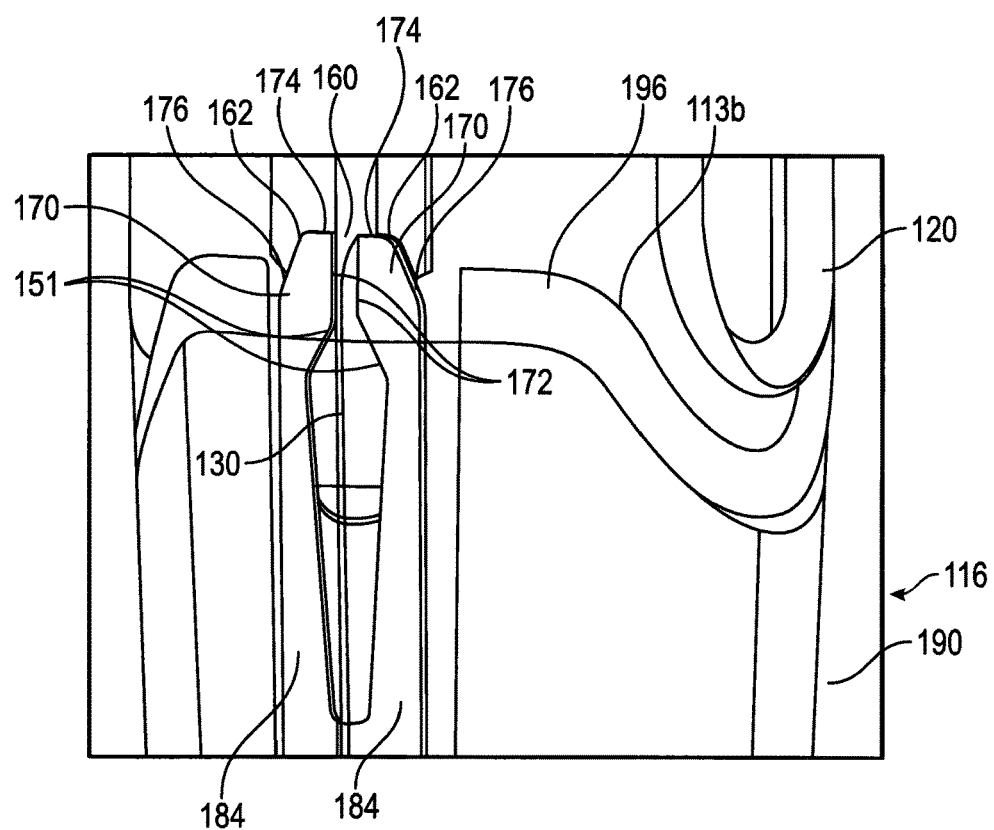

In this embodiment, the cap 116 includes an outer body 190 and an insert 180, as shown in FIGS. 9A and 9B. The outer body 190 is generally cylindrical in shape. The insert 180 comprises a forward portion 182 and two pairs of flexible arms 184 which extend rearwardly from the insert forward portion 182 (as shown in FIGS. 9A and 9B). To assemble the cap, the insert 180 is mounted into a forward end of the outer body 190, engaging elements 181, 191 are provided on the two cap components which engage to hold the two components together once assembled. When assembled, the forward portion 182 forms a forward end of the cap 116. As shown in FIGS. 8A and 8B, the rear tip sections of the arms 184 extend rearwardly from the outer body rear edge sections 192.

When the cap 116 is fitted onto the housing 110, rear edge sections 192 of the cap outer body 190 contact forward abutment surfaces 113 on the rear body 112.

The rear body 112 includes two projecting portions 113a which are provided on diametrically opposite sides, on opposite sides of the large diameter of the oval cross-section, and which project forwardly of the forward abutment surfaces 113. Two corresponding recesses 194 are provided on the cap outer body 190; the recesses 194 extending forwardly of the outer body rear edge sections 192. When the cap 116 is fitted onto the housing 110 the projection portions 113a are located within the recesses 194 (as shown, for example, in FIG. 5A).

The rear body 112 portion includes two cut-outs which acts as viewing window 120 through which at least a part of a syringe or cartridge (not shown in FIGS. 5A and 5B) mounted inside the housing 110 can be viewed. The viewing windows 120 are provided on diametrically opposite sides of the large diameter of the oval cross-section.

As shown in FIGS. 5B and 7B, two outwardly projecting protrusions 130 are provided on the outer surface of the front body 114. The protrusions 130 are provided on diametrically opposite sides of the front body 114 and they extend outwardly in a generally radial direction. In this embodiment they are provided at opposite sides of the small diameter of the oval cross-section of the front body 114.

The cap insert 180 includes two slots 150 formed between the pairs of arms 184. Each slot 150 includes two side walls 151 which extend rearwardly and define: a narrow neck portion 152 (which extends from the outer body rear edge when the cap is assembled), an elongate locating portion 154 having a maximum width greater than that of the neck 152, and an intermediate portion 156 joining the neck and locating portions 152, 154. The neck portion 152 extends substantially longitudinally and expands out (intermediate portion 154) forwardly into the locating portion 156. When the cap 116 is mounted (FIGS. 1A and 3A), one of the outwardly projecting protrusions 130 is located within the locating portion 154. The slot locating portion 156 is longer than the protrusion 130 in a longitudinal direction, this means that when the cap 116 is mounted onto the housing 110, the slot 150 extends rearwardly beyond the protrusion 130.

The rear body 112 has two forward facing cavities 160 which extend rearwardly from the forward abutment surface 113 of the rear body 112 . . . . The cavities 160 are formed by a recess or undercut in the rear body forward portion 12a (see FIG. 2B). Each cavity 160 includes two angled side walls 162 extending rearwardly from the rear body abutment surface 113.

As shown in FIGS. 8A and 8B, the rear tip sections of the arms 184 form engaging arms 170 which extend rearwardly from the outer body rear edge sections 192 on either side of the slot 150 when the insert 180 is mounted into the outer body 190. Each engaging arm 170 includes a first wall 172 extending continuously from a side wall 151 of the slot 150, a tip 174, and a second wall 176 which is sloped or angled from the tip 174 to the outer body rear edge 192.

When the cap 116 is mounted onto the housing, the second wall 176 forms a rearward facing engagement surface which engages with a corresponding forward facing mating surface formed by a cavity side wall 162. The engaging arms act 170 as resiliently deformable portions which are urged together by the cavity side walls 162 when the cap 116 is urged rearward on the housing (described in more detail below).

The cap outer body 190 includes reduced diameter elements 196 extending rearwardly from the rear edge of the recesses 194. The projecting portions 113a on the rear body portion 112 include undercuts 113b.

To mount the cap 116 onto the housing 110, the slots 150 are aligned with the protrusions 130. As cap 116 is pushed onto the housing, the slots 150 are pushed into engagement with the forward end of the protrusions 130, the slot necks 152 are opened outwards allowing the cap 116 to move rearwards. The cap 116 is pushed rearwards until the rear edge sections 192 of the cap outer body 190 contact the rear body abutment surface 113. When the cap 116 is in the mounted position, the protrusions 130 are fully located within the slot locating portions 156, the engagement arms 170 are located within the cavity 116 and the reduced diameter portions 196 are located within the cap undercuts 113b.

When the device 101 is subject to impact forces, the cap 116 is retained on the housing 110 in a similar way to the earlier embodiment.

If the device 1 is subjected to an impact force that urges the cap and housing together, the cap 116 is urged rearwardly against the rear body portion 112 (and the rear body may be urged forward by inertia). As such, the engagement surfaces 176 on the engagement arms 170 are urged against forward facing mating surfaces 162 in the cavity 116. This prevents the side walls 151 of the slot 150 from splaying outward which means that the protrusions 130 are firmly retained within the slots 150.

If the device 101 is subjected to an impact force which causes an internal force generated within the housing urging the forward body 114 forwards, a forward edge of the forward body 114 contacts rearwardly projecting ribs 186 provided on the end inner surface of the cap insert 182. This prevents the forward body 114 from moving further forward relative to the cap. In this embodiment, four ribs are provided equispaced around a circumference of the end surface insert 182. However, it will be appreciated that any suitable number of ribs or other formations may be provided to contact with the forward edge of the forward body.

The cap 116 is removed from the housing 110 by pulling rearwards. The rear tapered edge of the projections 130 engage and splay the flexible arms 184 outwards allowing the protrusion 130 to pass through the neck 152.

Since the insert 180 is mounted within the outer body 190, the slot 150 and flexible arms 184 of this embodiment are not visible to the user.

In another embodiment (not shown in the figures), the cap comprises three components: an outer body and two leg inserts, each leg insert including a pair of flexible arms and a slot formed between the two arms. The cap is assembled by mounting the two leg inserts inside the outer body. Once assembled, this cap substantially resembles the cap above of the second embodiment and functions in substantially the same way.

Although the invention has been described above with reference to preferred embodiments, it will be appreciated that various changes or modifications may be made without departing from the scope of the invention as defined in the appended claims. For example, the housing may be provided with a single forward facing cavity, and the cap may be provided with a single pair of rearwardly extending engagement arms. Further, the housing and/or cap may be provided with two viewing windows on opposite sides of the device. Alternatively, the device may not include a viewing window.

The injection device may include a delivery mechanism which is substantially of the type disclosed in the applicant's application WO2012/085580A1. It will, however, be appreciated that embodiments of the invention may be utilised with various known types of injection device. In particular, the invention is not limited to any particular delivery mechanism (and as such the delivery mechanism is not described herein) but typically, the delivery mechanism may include a plunger which is held in an initial latched position against the force of a drive spring, the plunger being released by the trigger arrangement to allow the plunger to be driven forwardly by the drive spring.

The invention claimed is:

1. An injection device comprising:
   an elongate housing; and
   a cap removably mounted over a forward end of the elongate housing, the cap comprising at least one slot extending forwardly from a rear edge, the at least one slot being configured to engage with an outwardly projecting protrusion on an outer surface of the elongate housing when the cap is mounted on the elongate housing,
   wherein a rearward portion of the cap includes rearwardly extending engagement features provided on each side of the at least one slot, the rearwardly extending engagement features being configured to locate within a cavity in the elongate housing when the cap is mounted on the elongate housing,
   wherein the cavity is provided with corresponding surfaces which align with the rearwardly extending engagement features to move the rearwardly extending engagement features together to reduce a width of the at least one slot and grip the protrusion upon location within the cavity and to prevent, or limit, side walls of the at least one slot from splaying outwardly when the rearwardly extending engagement features of the cap are located within the cavity, so as to hold the outwardly projecting protrusion within the at least one slot.

2. An injection device comprising:
   a housing; and
   a cap removably mounted over a forward end of the housing, the cap comprising at least one slot extending forwardly from a rear edge of the cap, the at least one slot being configured to engage with an outwardly projecting protrusion provided on an outer surface of the housing when the cap is mounted on the housing,
   wherein a rearward portion of the cap comprises portions on opposing sides of the at least one slot, at least one portion being resiliently deformable,
   the housing further comprises forward facing mating surfaces aligned with rearward facing engagement surfaces on the at least one resiliently deformable portion when the cap is mounted thereon, and
   wherein the forward facing mating surfaces and the rearward facing engagement surfaces of the at least one resiliently deformable portion are profiled such that when the forward facing mating surfaces and the rearward facing engagement surfaces are urged together, the at least one resiliently deformable portion is cammed inwardly relative to the at least one slot to restrict or reduce an effective width of the at least one slot and thereby grip the protrusion.

3. An injection device according to claim 1, wherein the at least one slot extends rearwardly beyond the protrusion when the cap is mounted on the elongate housing.

4. An injection device according to claim 2, wherein the rearward facing engagement surfaces on the cap each have a sloped profiles, and the forward facing mating surfaces on the housing have a corresponding sloped profile, so that as the cap is mounted onto the housing and pushed rearward, the forward facing mating surfaces and the rearward facing engagement surfaces are urged together.

5. An injection device according to claim 1, wherein the cap includes two engaging arms which extend rearwardly from the rear edge of the cap on opposing sides of the at least one slot, and each arm has an first surface extending from the at least one slot and a second, outer sloped surface.

6. An injection device according to claim 1, wherein the at least one slot includes a rear neck portion extending from the rear edge of the cap, leading to a locating portion having a maximum width greater than that of the rear neck portion, and wherein the outwardly projecting protrusion has a maximum width which substantially corresponds to the maximum width of the at least one slot locating portion.

7. An injection device according to claim 1, wherein the outwardly projecting protrusion is elongate and includes a rear portion which projects further outwards from the elongate housing than a forward portion.

8. An injection device according to claim 1, wherein the insert portion includes a forward portion and the rearwardly extending engagement features comprise two engaging arms, which extend rearwardly from the forward portion, and wherein opposing surfaces of the two engaging arms form the at least one slot, and each arm has a first surface extending from the at least one slot and a second, outer sloped surface.

9. An injection device according to claim 1, wherein the at least one slot includes a rear neck portion extending forward from a rear tip of the insert portion, leading to a locating portion having a maximum width greater than that of the rear neck portion, and wherein the outwardly projecting protrusion has a maximum width which substantially corresponds to the maximum width of the locating portion.

10. An injection device according to claim 2, wherein housing includes a rear body portion and a front body portion, wherein a front portion of the rear body portion is mounted-over a rear end of the front body portion, the outwardly projecting protrusion is provided on the front body portion and the forward facing mating surfaces are provided on the rear body portion.

11. An injection device according to claim 10, wherein the rear edge of the cap contacts a forward abutment surface on the rear body portion when the cap is mounted on the housing.

12. An injection device according to claim 11, wherein the rear edge of the cap is provided with an undercut on both sides of the at least one slot, and the rear body portion is provided on both sides of a cavity, with reduced diameter projections extending forwardly from the forward abutment surface and configured such that when the cap is mounted on the housing, the reduced diameter projections locate within the undercut on both sides of the at least one slot.

13. An injection device according to claim 12, wherein engaging arms extend rearwardly from the rear of the undercut, and wherein the cavity includes two side walls, and the reduced diameter projections extend forwardly from the two side walls of the cavity.

14. An injection device according to claim 1, wherein the cap is provided with two slots extending forwardly from the rear edge of the cap; and the outer surface of the elongate housing is provided with two corresponding outwardly projecting protrusions; such that each slot engages with one of the outwardly projecting protrusions when the cap is mounted on the elongate housing.

15. An injection device according to claim 1, wherein the elongate housing includes a rear body portion and a front body portion, the rear body portion being slideable relative to the front body portion in order to activate delivery of a medicament and/or to disengage an interlock.

16. An injection device according to claim 1, wherein the elongate housing and the cap include first and second cut-away regions, which when the cap is mounted on the elongate housing, are aligned to define a viewing window through which at least a part of a syringe or cartridge mounted inside the elongate housing can be viewed.

17. An injection device according to claim 2, wherein the housing includes a cut-away region, which defines a viewing window through which at least a part of a syringe or cartridge mounted inside the housing can be viewed.

18. An injection device according to claim 17, wherein the cap includes a reward facing recess and the housing includes a forward projecting portion, which engages with the recess when the cap is mounted on the housing, and wherein the cut-away region is provided at least partially in the forward projecting portion.

* * * * *